United States Patent
Dominguez et al.

(10) Patent No.: US 8,707,962 B2
(45) Date of Patent: Apr. 29, 2014

(54) DEVICE FOR PROTECTING AN AREA OF THE HUMAN BODY

(75) Inventors: Jean-Pierre Dominguez, Charpfey (FR); Damien Millet, Valence (FR); Jean-Claude Millet, Valence (FR)

(73) Assignee: Millet Innovation, Loriol sur Drome (FR)

( * ) Notice: Subject to any disclaimer, the term of this patent is extended or adjusted under 35 U.S.C. 154(b) by 27 days.

(21) Appl. No.: 13/197,302

(22) Filed: Aug. 3, 2011

(65) Prior Publication Data
US 2012/0024300 A1 Feb. 2, 2012

Related U.S. Application Data

(63) Continuation of application No. PCT/IB2009/007628, filed on Nov. 30, 2009.

(30) Foreign Application Priority Data

Feb. 13, 2009 (FR) ...................................... 09 00663

(51) Int. Cl.
*A61F 5/37* (2006.01)
*A61F 13/00* (2006.01)
*A61K 9/70* (2006.01)
*A61L 15/00* (2006.01)
*A61L 15/16* (2006.01)
*A61F 13/02* (2006.01)

(52) U.S. Cl.
USPC ........... 128/889; 128/846; 128/888; 424/443; 424/445; 424/447; 424/448; 602/41; 602/42; 602/43; 602/44; 602/45; 602/52; 602/54; 602/58

(58) Field of Classification Search
USPC ............ 602/41–45, 52, 54, 58; 424/443, 445, 424/447, 448; 128/846, 888, 889
See application file for complete search history.

(56) References Cited

U.S. PATENT DOCUMENTS

| 4,655,767 A | 4/1987 | Woodard et al. |
| 2005/0113732 A1 | 5/2005 | Lawry |

FOREIGN PATENT DOCUMENTS

| EP | 0300620 A1 | 1/1989 |
| EP | 1452156 A1 | 9/2004 |
| FR | 2712487 A1 | 5/1995 |
| FR | 2904932 A1 | 2/2008 |
| WO | 0053139 A1 | 9/2000 |

OTHER PUBLICATIONS

Int'l Search Report issued Feb. 11, 2010 in Int'l Application No. PCT/IB2009/007628; Written Opinion.

*Primary Examiner* — Patricia Bianco
*Assistant Examiner* — Brandon L Jackson
(74) *Attorney, Agent, or Firm* — Panitch Schwarze Belisario & Nadel LLP

(57) ABSTRACT

A device for protecting an area of skin of a human body includes a plate. The plate includes a first face covered by an external layer and a second face opposite the external layer. The second face is configured to be applied onto an area of skin to be protected. The plate also includes a protective part made of a polymer gel and at least one adhesive part made of a polymer gel. The protective part is configured to ensure mechanical protection of the area to be protected and the adhesive part is configured to come into contact with the skin. The adhesive part has an adhesive power greater than an adhesive power of the protective layer to hold the plate on the area to be protected.

10 Claims, 2 Drawing Sheets

DEVICE FOR PROTECTING AN AREA OF THE HUMAN BODY

CROSS-REFERENCE TO RELATED APPLICATIONS

This application is a Continuation of International Application No. PCT/IB2009/007628, filed Nov. 30, 2009, which was published in the French language on Aug. 19, 2010, under International Publication No. WO 2010/092428 A1 and the disclosure of which is incorporated herein by reference.

BACKGROUND OF THE INVENTION

The present invention relates to the protection of an area of the skin particularly in order to prevent bedsores and/or eschars. More generally, preferred embodiments of the present invention aim to mechanically protect and moisturize a relatively large area of the skin, and particularly an area of the skin weakened for example by pathologies such as psoriasis or eczema, or by a recent scar.

One well-known method involves using polymer gel-based plates such as silicone gel or hydrogel-based plates to protect skin or for load distribution. Now, the constraints related to the desired effect of the plate on the skin often prove contradictory with the constraints related to holding the plate on the area to be protected or to the handling, transport and storage of the plate.

For example, to ensure a load distribution function, one well-known method involves using a plate made of a relatively hard silicone gel of PDMS (polydimethylsiloxane) type. Plates made of a silicone gel less hard, but more adhesive, are for example described in documents FR 2 712 487 and FR 2 904 932. However, silicone gels of this type are not very adhesive, and in any case, not sufficiently adhesive to naturally remain in place on the area to be protected. Furthermore, to ensure sufficient load distribution, the plate must have a thickness of several millimeters, which is not possible if the plate must be held on the area to be protected. Indeed, the thicker the plate edges are, the more they may get caught, thus resulting in the plate being pulled off.

Some documents, for example, documents U.S. Pat. No. 4,655,767 and WO 00/53 139, describe a method of dissociating the treatment or protection function from the function of holding onto the skin, using an adhesive strip onto which the element ensuring the treatment or protection function is arranged. However, this solution is not appropriate, particularly when the surface to be protected is relatively large, and when the skin to be protected is weakened. Indeed, people who are likely to have bedsores often have weakened skin that is poorly vascularised and sometimes dry. Traditional adhesives on a polyurethane film might be aggressive for the skin (pulling off pieces of skin or hairs) when removing the film. This aggressiveness is all the more significant and penalizes skin more when the adhesive surface is large. It is also essential to avoid all risk of allergy, which is frequent with traditional solutions.

It is thus desirable to produce a protection device capable of protecting a relatively large area of skin, with no risk of allergy, and capable of sticking to the skin with no risk of untimely removal and mistreatment of the skin when removing the device.

BRIEF SUMMARY OF THE INVENTION

Some preferred embodiments relate to a device for protecting an area of the skin of the human body, comprising a plate comprising one face covered by an external layer, and one face opposite the external layer, intended to be applied onto an area of the skin to be protected. According to one preferred embodiment, the plate comprises a protective part comprising a polymer gel, and at least one adhesive part comprising a polymer gel and intended to come into contact with the skin, the protective part being configured to ensure mechanical protection of the area to be protected, the polymer gel forming the adhesive part having an adhesive power greater than that forming the protective part to hold the plate on the area to be protected.

According to one preferred embodiment, the protective part of the plate has a thickness between 1 and 4 mm.

According to one preferred embodiment, the adhesive part has a thickness between 0.2 and 0.5 mm.

According to one preferred embodiment, the protective part is produced by polymerizing at least partially a mixture comprising: approximately 15% of dimethyl-vinyl-terminated polydimethylsiloxane having a viscosity greater than 20,000 mPa·s, approximately 25% of dimethyl-vinyl-terminated polydimethylsiloxane having a viscosity between 200 and 20,000 mPa·s, approximately 45% of trimethyl-terminated polydimethylsiloxane having a viscosity lower than 100 mPa·s, approximately 12% of trimethylsiloxy-treated pyrogenic silica, and approximately 3% of dimethyl-hydrogen-terminated co-polydimethylsiloxane-polymethyl-hydrogen-siloxane.

According to one preferred embodiment, the protective part is produced by polymerizing at least partially a mixture comprising: approximately 15% of dimethyl-vinyl-terminated polydimethylsiloxane having a viscosity greater than 20,000 mPa·s, approximately 25% of dimethyl-vinyl-terminated polydimethylsiloxane having a viscosity between 200 and 20,000 mPa·s, approximately 25% of trimethyl-terminated polydimethylsiloxane having a viscosity lower than 100 mPa·s, approximately 20% of trimethyl-terminated polydimethylsiloxane having a viscosity greater than 20,000 mPa·s, approximately 12% of trimethylsiloxy-treated pyrogenic silica, and approximately 3% of dimethyl-hydrogen terminated co-polydimethylsiloxane-polymethyl-hydrogen-siloxane.

According to one preferred embodiment, the adhesive part is made of Epithélium 28®.

According to one preferred embodiment, the external layer is made of fabric and is glued onto one face of the protective part and of the adhesive part.

According to one preferred embodiment, the fabric forming the external layer is elastic.

According to one preferred embodiment, the external layer is made of a non-adhesive silicone gel with a thickness between 0.2 and 0.4 mm or of a silicone glue with a thickness between 0.05 and 0.4 mm.

According to one preferred embodiment, each adhesive part has a width between 5 and 60 mm and an adhesive power in the order of 130 to 140 g/cm$^2$.

Some preferred embodiments also relate to a method for manufacturing a device for protecting an area of the skin of the human body. According to one preferred embodiment, the method comprises steps of forming a plate comprising a protective part comprising a polymer gel and at least one adhesive part comprising a polymer gel, intended to come into contact with the skin, the protective part being configured to ensure mechanical protection of the area to be protected, the polymer gel forming the adhesive part having an adhesive power greater than that forming the protective part to hold the plate on the area to be protected.

According to one preferred embodiment, the method comprises steps of forming the adhesive part using a first liquid mixture deposited on a medium, and of forming the protective part using a second liquid mixture deposited on the medium, the first mixture and the second mixture partially mixing in an interface area, before full polymerization of both mixtures.

According to one preferred embodiment, the second mixture comprises: approximately 15% of dimethyl-vinyl-terminated polydimethylsiloxane having a viscosity greater than 20,000 mPa·s, approximately 25% of dimethyl-vinyl-terminated polydimethylsiloxane having a viscosity between 200 and 20,000 mPa·s, approximately 45% of trimethyl-terminated polydimethylsiloxane having a viscosity lower than 100 mPa·s, approximately 12% of trimethylsiloxy-treated pyrogenic silica, and approximately 3% of dimethyl-hydrogen terminated co-polydimethylsiloxane-polymethyl-hydrogen-siloxane.

According to one preferred embodiment, the second mixture comprises: approximately 15% of dimethyl-vinyl-terminated polydimethylsiloxane having a viscosity greater than 20,000 mPa·s, approximately 25% of dimethyl-vinyl-terminated polydimethylsiloxane having a viscosity between 200 and 20,000 mPa·s, approximately 25% of trimethyl-terminated polydimethylsiloxane having a viscosity lower than 100 mPa·s, approximately 20% of trimethyl-terminated polydimethylsiloxane having a viscosity greater than 20,000 mPa·s, approximately 12% of trimethylsiloxy-treated pyrogenic silica, and approximately 3% of dimethyl-hydrogen-terminated co-polydimethylsiloxane-polymethyl-hydrogen-siloxane.

According to one preferred embodiment, the two liquid mixtures are deposited on an unwinding medium so as to form strips, the first mixture being deposited on the medium so as to form two adhesive strips between which the second mixture is deposited to form the protective part in strip form.

According to one preferred embodiment, the thickness and the width of each of the protective and adhesive parts are adjusted by a scraper and lateral guides.

According to one preferred embodiment, the method comprises a step of fixing, onto one face of the plate opposite the face intended to come into contact with the skin, a non-adhesive external layer.

According to one preferred embodiment, the external layer is made of a fabric glued onto the plate.

According to one preferred embodiment, the external layer is made of a non-adhesive polymer gel with a thickness between 0.2 and 0.4 mm or of a silicone glue with a thickness between 0.05 and 0.4 mm.

According to one preferred embodiment, the face of the plate intended to come into contact with the skin is covered by a protective film.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
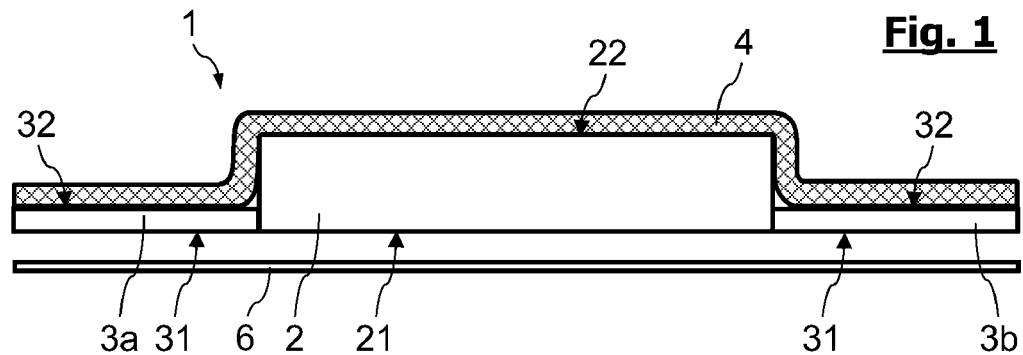
FIG. 1 schematically represents a protection device according to a preferred embodiment of the present invention.

FIG. 1 represents a protection device according to one preferred embodiment of the present invention. In FIG. 1, the protection device is in the form of a plate 1 comprising a central part 2 provided to cover an area to be protected on the skin of the human body, and lateral parts 3a, 3b comprising a rear face 32 and an adhesive front face 31 intended to come into contact with the skin and to hold the plate 1 on the area to be protected. The central part 2 has a front face 21 provided to come into contact with the skin, a rear face 22 and a thickness suited to the mechanical protection properties desired. The thickness of the lateral parts 3a, 3b may be smaller than that of the central part 2. The lateral parts are integral with the central part so that the front face 21 of the central part is located substantially in the same plane as the front face 31 of the lateral parts. The rear faces 22 and 32 of the central part and of the lateral parts are covered by a protective layer 4.

The lateral parts 3a, 3b can be made of a cross-linked silicone gel to be sufficiently adhesive, for example of Epithélium 28® marketed by the company Millet Innovation. This material is a very high tack material, with no risk of pulling off the skin or hairs when removing the protection device, and no risk of causing allergies. The thickness of the lateral parts 3a, 3b can be relatively low, for example between 0.2 and 0.5 mm.

The central part 2 can be made of a polymer gel, for example a silicone gel. If the central part 2 must ensure mechanical protection, it is made of a cross-linked silicone gel so that it is relatively hard and thus little adhesive. The central part 2 has a thickness which can be about ten times greater than that of the lateral parts 3a, 3b.

In an application to prevent bedsores, the central part 2 is made of a silicone gel, having a thickness between 1 and 4 mm and rigidity and viscosity properties and a cushioning factor capable of limiting the underlying shear and maintaining microcirculation in the protected tissues, despite the presence of pressure. For this purpose, at 35° C., the silicone gel can have a rigidity or elastic component varying from approximately 11,000 to 20,000 Pa, a viscosity or cushioning component varying from approximately 700 to 8,000 Pa and a cushioning factor varying from approximately 0.06 to 0.38, when a shear rate varies between 0 and 100 rd/s.

These properties are for example obtained when the central part 2 is produced by polymerizing at least partially one or the other of two mixtures the content of which is summarized in Table 1 below:

TABLE 1

| Component | Mixture 1 | Mixture 2 |
|---|---|---|
| dimethyl-vinyl-terminated polydimethylsiloxane with a viscosity greater than | approx. 15% | approx. 15% |

TABLE 1-continued

| Component | Mixture 1 | Mixture 2 |
|---|---|---|
| 20,000 mPa · s dimethyl-vinyl-terminated polydimethylsiloxane with a viscosity between 200 and 20,000 mPa · s | approx. 25% | approx. 25% |
| Trimethyl-terminated polydimethylsiloxane with a viscosity lower than 100 mPa · s | approx. 45% | approx. 25% |
| trimethyl-terminated polydimethylsiloxane with a high viscosity greater than 20,000 mPa · s | 0 | approx. 20% |
| trimethylsiloxy-treated pyrogenic silica | approx. 12% | approx. 12% |
| dimethyl-hydrogen-terminated co-polydimethylsiloxane-polymethyl-hydrogen-siloxane | approx. 3% | approx. 3% |

The partial polymerization of the mixtures 1 and 2 can be obtained using a platinum-vinyl siloxane complex catalyst. When it is produced using the mixtures 1 and 2, the central part 2 has an adhesiveness between 100 and 115 g/cm2.

The protective layer 4 can be made of fabric, for example an elastic fabric, such as elasthane polyamide fabric.

A protective film 6 can be arranged on the faces 21 and 31 intended to come into contact with the skin to enable the protection device 1 to be stored and transported, the protective film being removed just before applying the device 1 onto the skin.

Figure 2:
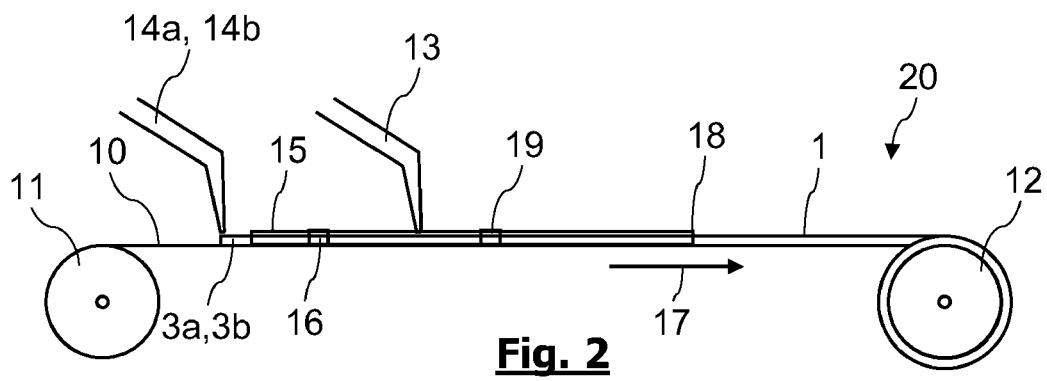
FIG. 2 schematically represents a side view of a machine for manufacturing the protection device, in accordance with a preferred embodiment of the present invention.
Figure 3:
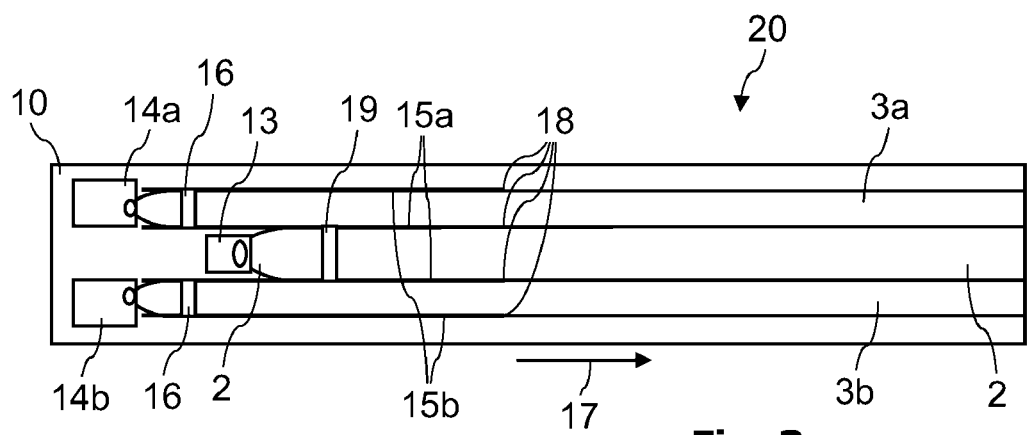
FIG. 3 is a schematic top view of the manufacturing machine represented in FIG. 2.

FIGS. 2 and 3 represent a manufacturing machine 20 for manufacturing the protection device. The machine 20 enables plates 1 to be manufactured in the form of a continuous strip. The machine 20 comprises an anti-adhesive support strip 10, for example made of PVC, which is unwound on one side of a coil 11 and wound on the other side around another coil 12. Between the two coils 11, 12, the strip 10 moves substantially horizontally in an unwinding direction indicated by the arrow 17. The machine 20 comprises at least two lateral nozzles 14a, 14b and one or more central nozzles 13 which can be installed at a certain distance from the lateral nozzles towards the coil 12. The nozzles 14a, 14b enable the lateral parts 3a, 3b of the plate 1 to be formed. For this purpose, the nozzles 14a, 14b deposit on the strip 10 a first mixture of silicone oils between lateral, internal 15a and external 15b guides arranged longitudinally and vertically on the strip 10. The nozzle 13 enables the central part 2 of the plate 1 to be formed. For this purpose, the nozzle 13 deposits between the two internal guides 15a a second mixture of silicone oils. The flow rate of the nozzles 13, 14a, 14b is suited to the cross-linking time of the mixtures, to the unwinding speed of the strip 10 and to the dimensions of the central 2 and lateral 3a, 3b parts.

The manufacturing machine 20 also comprises scrapers 16, 19 arranged horizontally above the strip 10 to adjust the thickness of the lateral parts 3a, 3b and of the central part 2. The combination of the guides 15a, 15b and of the scrapers enables the respective widths and thicknesses of the central 2 and lateral 3a, 3b parts to be finely adjusted.

The first mixture is designed to obtain specific spreading conditions on the strip 10, a certain polymerization time and appropriate final viscoelastic and adhesive properties. The second mixture is designed to obtain viscoelastic properties corresponding to the function to be obtained from the protection device to be produced. The first and second mixtures contain, for example, PDMS (polydimethylsiloxane).

At the downstream end 18 (relative to the unwinding direction 17) of the guides 15a, 15b, the lateral parts 3a, 3b the viscosity of which has become higher than that of the second mixture partly retain the less viscous central part 2. As the central part 2 is thicker than the lateral parts 3a, 3b, the second mixture tends to cover the lateral parts 3a, 3b in a narrow interface area. In this interface area, the silicone oils not yet polymerized of the two mixtures tend to mix. After polymerization, complete continuity is thus obtained between the central part and the lateral parts. It shall also be noted that the first mixture forming the lateral parts 3a, 3b polymerizes faster than the second mixture forming the central part 2.

Downstream from the guides 15a, 15b, the polymerization of the two mixtures continues for example in a polymerization tunnel (not represented) which can be heated to speed up the polymerization and thus the production rate of the protection device. At the end of the polymerization, the assembly comprising the strip plate 1 and the support strip 10 is wound onto the coil 12. The coil 12 is then put in a machine for continuously gluing the external layer 4 onto the faces 22 and 32 of the central and lateral parts, and for applying the protective film 6 onto the opposite faces 21 and 31.

The plate 1 has a sufficient adhesive power when the lateral parts 3a, 3b have a width between 5 and 60 mm and an adhesive power in the order of 130 to 140 g/cm2.

Furthermore, it shall be noted that the first mixture can alternatively be deposited on the support strip 10 after the second mixture.

Figure 4:
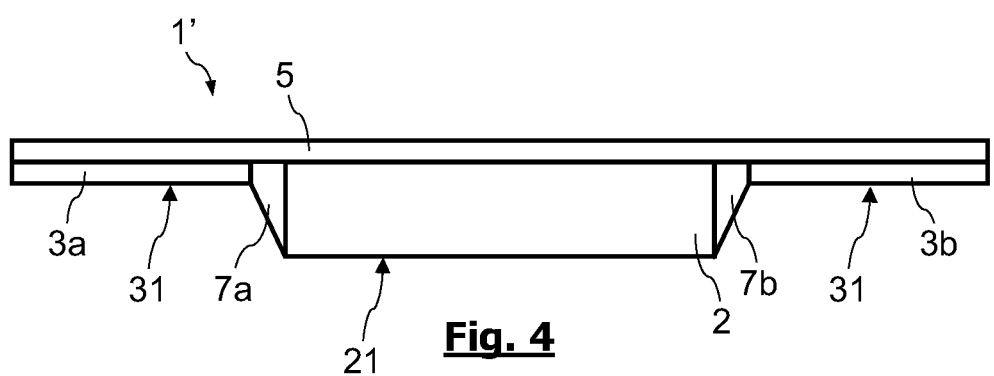
FIG. 4 schematically represents a protection device according to another preferred embodiment of the present invention.

FIG. 4 represents a protective plate 1' according to another preferred embodiment of the present invention. The plate 1' differs from the plate 1 represented in FIG. 1 in that the layer of fabric 4 is replaced with a relatively hard and non-adhesive layer of polymer gel 5. The layer 5 can be formed in the manufacturing machine before the lateral 3a, 3b and central 2 parts, the first and second mixtures being poured onto the layer 5 after at least partially polymerizing the latter, so as to obtain a mixture of the layers in interface areas and therefore complete continuity between the layer 5 and the central 2 and lateral 3a, 3b parts. Thus, the lateral parts 3a, 3b are linked to the central part 2 by junction areas 7a, 7b made of a different material. The layer 5 can be made of a silicone gel, of the Epithélium 26® type for example marketed by the company Millet Innovation, and has a thickness between 0.2 and 0.5 mm. The protective layer 5 may also be made of a thin layer of silicone glue such as a glue marketed to produce assemblies of silicones, the adhesiveness of which has little or no effect on the support strip 10. The layer 5 can therefore be even thinner and be practically transparent.

Figure 5:
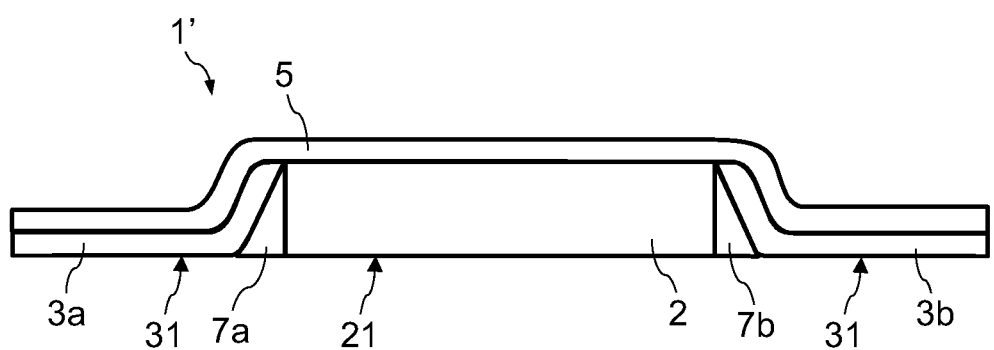
FIG. 5 schematically represents the protection device in FIG. 4 in a ready-to-use configuration, in accordance with a preferred embodiment of the present invention.

FIG. 5 represents the plate 1' in a ready-to-use configuration, or when applying the protective film 6 onto the faces 21 and 31 of the central 2 and lateral 3a, 3b parts. In the configuration represented in FIG. 4, the faces 21 of the central part 2 and 31 of the lateral parts are not in the same plane due to the manufacturing method implemented. In the configuration represented in FIG. 5, the lateral parts 3a, 3b and the layer 5 have been distorted so that the faces 31 are at least partly in the plane of the face 21.

The strip obtained by the machine 10 is used by first of all cutting a piece of the strip to a length corresponding to that of the area of skin to be protected, to obtain an individual plate 1 or 1'. The protective film 6 is then removed from the plate which is then applied onto the area to be protected. The adhesiveness and the fineness of the lateral parts 3a, 3b of the plate 1 or 1' enable an excellent hold of the plate on the skin. Furthermore, when the central part 2 is made of a silicone gel sufficiently thick and hard to ensure good load distribution, it proves to be capable of absorbing a substantial part of the shear and compression stress that the tissues in the vicinity of a bone can undergo. The central part 2 is also capable of reducing the repeated dynamic stress on the tissues which results in fatigue of the skin and more deeply of the tissues and vessels. It can therefore also maintain the irrigation of the tissues. The adhesiveness of the central part, although it is low, also proves to be sufficient to significantly limit friction between the skin and its environment. Thus, the central part 2 is efficient to prevent the formation of bedsores. This protective feature is strengthened by the fact that the silicone gel is relatively waterproof and thus favors the moisturizing of the skin in contact by sweating. The result is an improvement in the superficial vascularization of the skin in contact, which tends to prevent bedsores. It shall be noted that the plate 1 or 1' can easily be removed from the skin, with no risk of injuries even if the skin is weakened. The plate 1 or 1' can also be easily cleaned to be reused, as cleaning does not affect the adhesive feature of the lateral parts 3a, 3b.

The protection device previously described can also be used for other purposes, for example to heal keloid scars or to protect areas of the skin affected by psoriasis or eczema.

It will be understood by those skilled in the art that various alternative embodiments of the present invention are possible. In particular, the present invention is not limited to a protection device consisting of a strip to be cut. The protection device can be manufactured directly in the form of plates with different dimensions, by pouring appropriate quantities of the liquid mixtures into individual molds with mobile guides to separate the mixtures at the beginning of their polymerization.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A device for protecting an area of skin of a human body, the device being reusable and comprising:
    an external layer and a plate, the plate comprising:
        a protective part comprising a first polymer gel, the protective part having a first face covered by the external layer and an opposing second face configured to be applied onto an area of skin to be protected and to ensure mechanical protection thereof; and
        at least one adhesive part comprising a second polymer gel and laterally adjoining the protective part, the at least one adhesive part having a first face and an opposing second face configured to come into contact with the skin, the second face of the protective part and the second face of the at least one adhesive part lying in a common plane, the second polymer gel having an adhesive power greater than an adhesive power of the first polymer gel to hold the plate on the area of skin to be protected, the first and second polymer gels being mixed in a lateral interface zone between the protective part and the at least one adhesive part.

2. The device according to claim 1, wherein the external layer is made of fabric and is glued onto the first face of the protective part and first face of the at least one adhesive part.

3. The device according to claim 2, wherein the fabric forming the external layer is elastic.

4. The device according to claim 1, wherein the protective part of the plate has a thickness between 1 and 4 mm.

5. The device according to claim 1, wherein the adhesive part has a thickness between 0.2 and 0.5 mm.

6. The device according to claim 1, wherein the protective part is produced by at least partially polymerizing a mixture comprising:
    approximately 15% of dimethyl-vinyl-terminated polydimethylsiloxane having a viscosity greater than 20,000 mPa·s,
    approximately 25% of dimethyl-vinyl-terminated polydimethylsiloxane having a viscosity between 200 and 20,000 mPa·s,
    approximately 45% of trimethyl-terminated polydimethylsiloxane having a viscosity lower than 100 mPa·s,
    approximately 12% of trimethylsiloxy-treated pyrogenic silica, and
    approximately 3% of dimethyl-hydrogen-terminated co-polydimethylsiloxane-polymethyl-hydrogen-siloxane.

7. The device according to claim 1, wherein the protective part is produced by at least partially polymerizing a mixture comprising:
    approximately 15% of dimethyl-vinyl-terminated polydimethylsiloxane having a viscosity greater than 20,000 mPa·s,
    approximately 25% of dimethyl-vinyl-terminated polydimethylsiloxane having a viscosity between 200 and 20,000 mPa·s,
    approximately 25% of trimethyl-terminated polydimethylsiloxane having a viscosity lower than 100 mPa·s,
    approximately 20% of trimethyl-terminated polydimethylsiloxane having a viscosity greater than 20,000 mPa·s,
    approximately 12% of trimethylsiloxy-treated pyrogenic silica, and
    approximately 3% of dimethyl-hydrogen terminated co-polydimethylsiloxane-polymethyl-hydrogen-siloxane.

8. The device according to claim 1, wherein the adhesive part is made of a cross-linked silicone gel.

9. The device according to claim 1, wherein the external layer is made from one of a non-adhesive silicone gel having a thickness between 0.2 and 0.4 mm and a silicone glue having a thickness between 0.05 and 0.4 mm.

10. The device according to claim 1, wherein each adhesive part has a width between 5 and 60 mm and an adhesive power on the order of 130 to 140 g/cm$^2$.

* * * * *